(12) United States Patent
Arnold et al.

(10) Patent No.: US 11,642,074 B2
(45) Date of Patent: *May 9, 2023

(54) SEIZURE DETECTION DEVICE

(71) Applicants: KNOW BIOLOGICAL, INC., Milton, GA (US); National Technology & Engineering Solutions of Sandia, LLC, Albuquerque, NM (US)

(72) Inventors: Gary Stephen Arnold, Cumming, GA (US); Matthew Wallace Moorman, Albuquerque, NM (US); Joshua Jonathan Whiting, Albuquerque, NM (US)

(73) Assignees: Know Biological, Inc., Milton, GA (US); National Technology & Engineering Solutions of Sandia, LLC, Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/308,145

(22) Filed: May 5, 2021

(65) Prior Publication Data

US 2021/0251560 A1     Aug. 19, 2021

Related U.S. Application Data

(62) Division of application No. 16/874,229, filed on May 14, 2020, now Pat. No. 11,020,042.

(Continued)

(51) Int. Cl.
*A61B 5/00* (2006.01)
*A61B 10/00* (2006.01)
(Continued)

(52) U.S. Cl.
CPC .......... *A61B 5/4094* (2013.01); *A61B 5/0075* (2013.01); *A61B 5/443* (2013.01);
(Continued)

(58) Field of Classification Search
CPC ..... A61B 5/4094; A61B 5/443; A61B 5/6833; G01N 2030/025; G01N 30/00
See application file for complete search history.

(56) References Cited

U.S. PATENT DOCUMENTS

| 5,036,861 A | 8/1991 | Sembrowich et al. |
| 5,281,397 A | 1/1994 | Ligon et al. |

(Continued)

FOREIGN PATENT DOCUMENTS

| WO | 2020232349 | 11/2020 |
| WO | 2021050678 | 3/2021 |

OTHER PUBLICATIONS

Davis, The Investigation of Human Scent from Epileptic Patients for the Identification of a Biomarker for Epileptic Seizures, Florida International University, Oct. 31, 2017. (Year: 2017).*

(Continued)

*Primary Examiner* — Puya Agahi
(74) *Attorney, Agent, or Firm* — Taylor English Duma LLP

(57) ABSTRACT

A method of detecting a seizure includes collecting volatile organic compounds with a collector material of a collector; separating a mixture of the volatile organic compounds into its constituent chemicals with a gas chromatography column; ionizing the constituent chemicals to create ionized chemicals and detecting the ionized chemicals; and analyzing the ionized chemicals to identify seizure-indicative volatile organic compounds.

20 Claims, 2 Drawing Sheets

Related U.S. Application Data

(60) Provisional application No. 62/848,319, filed on May 15, 2019.

(51) Int. Cl.

| | |
|---|---|
| *G01N 30/64* | (2006.01) |
| *G01N 30/20* | (2006.01) |
| *G01N 30/80* | (2006.01) |
| *G01N 30/00* | (2006.01) |
| *G01N 30/02* | (2006.01) |
| *A61B 5/145* | (2006.01) |

(52) U.S. Cl.
CPC .......... *A61B 5/6831* (2013.01); *A61B 5/6833* (2013.01); *A61B 10/00* (2013.01); *G01N 30/00* (2013.01); *G01N 30/20* (2013.01); *G01N 30/64* (2013.01); *G01N 30/80* (2013.01); *A61B 5/14546* (2013.01); *A61B 2010/0083* (2013.01); *G01N 2030/025* (2013.01)

(56) References Cited

U.S. PATENT DOCUMENTS

| | | | |
|---|---|---|---|
| 6,666,907 | B1 | 12/2003 | Manginell et al. |
| 6,699,392 | B1 | 3/2004 | Manginell et al. |
| 7,118,712 | B1 | 10/2006 | Manginell et al. |
| 7,155,812 | B1 | 1/2007 | Peterson et al. |
| 10,151,732 | B1 | 12/2018 | Moorman et al. |
| 10,161,835 | B1 | 12/2018 | Moorman et al. |
| 11,020,042 | B2 | 6/2021 | Arnold et al. |
| 11,272,875 | B2 | 3/2022 | Arnold et al. |
| 11,559,246 | B2 | 1/2023 | Arnold et al. |
| 2007/0027383 | A1 | 2/2007 | Peyser et al. |
| 2008/0146890 | A1 | 6/2008 | Leboeuf et al. |
| 2011/0259081 | A1* | 10/2011 | Chou ................... G01N 30/463 73/23.42 |
| 2013/0328697 | A1 | 12/2013 | Lundy |
| 2016/0015315 | A1 | 1/2016 | Auphan et al. |
| 2016/0103104 | A1* | 4/2016 | Gianchandani ... B01L 3/502707 73/23.41 |
| 2016/0194590 | A1* | 7/2016 | Loboda ................... H01J 49/04 435/307.1 |
| 2017/0027482 | A1 | 2/2017 | Zilberstein et al. |
| 2017/0035622 | A1 | 2/2017 | Wang |
| 2017/0119279 | A1 | 5/2017 | Ahmad et al. |
| 2017/0209313 | A1 | 7/2017 | Letourneau et al. |
| 2017/0248524 | A1* | 8/2017 | Le ......................... A61B 5/6833 |
| 2018/0042585 | A1* | 2/2018 | Heikenfeld ......... G01N 33/48792 |
| 2018/0153451 | A1* | 6/2018 | Heikenfeld .......... A61B 10/0064 |
| 2018/0160909 | A1 | 6/2018 | Damania et al. |
| 2018/0256137 | A1* | 9/2018 | Heikenfeld .......... A61B 10/0064 |
| 2019/0021674 | A1 | 1/2019 | Brewer, Jr. et al. |
| 2019/0030230 | A1 | 1/2019 | Connor |
| 2019/0099009 | A1 | 4/2019 | Connor |
| 2019/0254641 | A1* | 8/2019 | Begtrup ............. A61B 5/14517 |
| 2020/0008756 | A1* | 1/2020 | Nishiyama ............. A61B 5/441 |
| 2020/0330011 | A1* | 10/2020 | Honore ................ A61B 5/1455 |
| 2020/0337594 | A1 | 10/2020 | Reddy |
| 2020/0359955 | A1 | 11/2020 | Arnold et al. |
| 2021/0085295 | A1 | 3/2021 | Fehr et al. |
| 2021/0282678 | A1* | 9/2021 | Haick ................... A61B 5/0803 |
| 2021/0321934 | A1 | 10/2021 | Arnold et al. |
| 2021/0338142 | A1 | 11/2021 | Arnold et al. |
| 2022/0142557 | A1 | 5/2022 | Arnold et al. |

OTHER PUBLICATIONS

Arnold, Gary Stephen; Notice of Allowance for U.S. Appl. No. 16/874,229, filed May 14, 2020, dated Apr. 27, 2021, 211 pgs.

Arnold, Gary Stephen; Requirement for Restriction/Election for U.S. Appl. No. 16/874,229, filed May 14, 2020, dated Mar. 3, 2021, 7 pgs.

Maa et al., Canine detection of volatile organic compounds unique to human epileptic seizure, (hllps://www.sciencedirect.com/science/article/pii/S1525505020308702), Epilepsy and Behavior, Dec. 23, 2020. (Year: 2020).

Zamkah et al., Identification of Suitable Biomarkers for Stress and Emotion Detection for Future Personal Affective Wearable Sensors, (hllps://www.ncbi.nlm.nih.gov/pmc/articles/PMC7235866/), Biosensors, Apr. 16, 2020. (Year: 2020).

Arnold, Gary Stephen; International Search Report and Written Opinion for PCT Application No. PCT/US20/33120, filed May 15, 2020, dated Aug. 19, 2020, 8 pgs.

Arnold, Gary Stephen; Requirement for Restriction/Election for U.S. Appl. No. 17/340,195, filed Mar. 7, 2021, dated Oct. 14, 2021, 6 pgs.

Arnold, Gary Stephen; Requirement for Restriction/Election for U.S. Appl. No. 17/242,441, filed Jan. 28, 2021, dated Sep. 1, 2021, 6 pgs.

Arnold, Gary Stephen; Final Office Action for U.S. Appl. No. 17/340,195, filed Jun. 7, 2021, dated Mar. 17, 2022, 20 pgs.

Arnold, Gary Stephen; Non-Final Office Action for U.S. Appl. No. 17/340,195, filed Jun. 7, 2021, dated May 26, 2022, 18 pgs.

Arnold, Gary Stephen; Non-Final Office Action for U.S. Appl. No. 17/568,799, filed Jan. 5, 2022, dated Mar. 31, 2022, 20 pgs.

Arnold, Gary Stephen; Applicant-Initiated Interview Summary for U.S. Appl. No. 17/340,195, filed Jun. 7, 2021, dated Aug. 1, 2022, 2 pgs.

Arnold, Gary Stephen; Notice of Allowance for U.S. Appl. No. 17/340,195, filed Jun. 7, 2021, dated Sep. 21, 2022, 20 pgs.

Arnold, Gary Stephen; Final Office Action for U.S. Appl. No. 17/568,799, filed Jan. 5, 2022, dated Jul. 27, 2022, 16 pgs.

Arnold, Gary Stephen; Applicant-Initiated Interview Summary for U.S. Appl. No. 17/340,195, filed Jun. 7, 2021, dated Dec. 27, 2021, 4 pgs.

Arnold, Gary Stephen; Non-Final Office Action for U.S. Appl. No. 17/340,195, filed Jun. 7, 2021, dated Nov. 26, 2021, 17 pgs.

Arnold, Gary Stephen; International Preliminary Report on Patentability for PCT Application No. PCT/US20/33120, filed May 15, 2020, dated Nov. 25, 2021, 7 pgs.

Arnold, Gary Stephen; Notice of Allowance for U.S. Appl. No. 17/242,441, filed Apr. 28, 2021, dated Nov. 12, 2021, 15 pgs.

Arnold, Gary Stephen; Notice of Allowance for U.S. Appl. No. 17/568,799, filed Jan. 5, 2022, dated Oct. 18, 2022, 12 pgs.

Arnold, Gary Stephen; Extended European Search Report for application No. 22176201.6, filed May 30, 2022, dated Oct. 13, 2022, 9 pgs.

Roodt, et al; Article entitled: "Human skin volatiles: Passive sampling and Go X GC-ToFMS analysis as a tool to investigate the skin microbiome and interactions with anthropophilic mosquito disease vectors", Journal of Chromatography B1097-1098 (2018) 83-93, 11 pgs.

\* cited by examiner

SEIZURE DETECTION DEVICE

CROSS-REFERENCE TO RELATED APPLICATIONS

The present application is a divisional of U.S. application Ser. No. 16/874,229, filed May 14, 2020, which claims the benefit of U.S. Provisional Application No. 62/848,319, filed May 15, 2019, both of which are hereby specifically incorporated by reference herein in their entireties.

STATEMENT OF GOVERNMENT INTEREST

This invention was made with government support under Contract No. DE-NA0003525 awarded by the United States Department of Energy/National Nuclear Security Administration. The government has certain rights in the invention.

TECHNICAL FIELD

This disclosure relates to medical devices. More specifically, this disclosure relates to a seizure detection device.

BACKGROUND

Epilepsy is the most common neurological disorder in the world after migraine, stroke, and Alzheimer's disease. It is a disorder of the central nervous system, not caused by an underlying, treatable medical condition, characterized by recurring periods of altered brain function caused by abnormal or excessive electrical discharges in the brain, resulting in what is commonly called a seizure. It is one of the world's oldest recognized health conditions, with recorded occurrences dating back to 4,000 BC.

Worldwide, there are nearly 65 million people who have epilepsy, with more than 3.5 million in the U.S. alone. Worldwide, there are 2.4 million new cases of epilepsy each year, with more than 150,000 new cases each year in the U.S. alone. Over a lifetime, more than one in twenty-six people with be diagnosed with the disease. Medication and medical intervention can control seizures in approximately two-thirds of patients, with the remaining one-third experiencing uncontrolled and unpredictable seizure episodes. There are estimated to be nearly one million deaths directly related to epilepsy each year worldwide, including some 50,000 deaths in the U.S each year.

Each year, approximately 80 people out of every 100,000 in the general population will experience new-onset seizures, and approximately 60% of these will have repeated episodes leading to the diagnosis of epilepsy. Misunderstanding, prejudice, and social humiliation have always surrounded epilepsy. This continues in most countries today and can significantly impact the quality of life for people with epilepsy.

The social consequences of epilepsy are often more impactful than the seizures themselves. The lack of predictability inherent in epilepsy is devastating. Never knowing when a seizure might strike imposes major limitations in family, social, educational, and vocational activities. In addition to the potential of serious injury from falls and other accidents during seizures, the societal stigma attached to epilepsy and its unpredictability that can cause significant demoralization, irritation, and anxiety. Frustratingly, studies have shown that increased anxiety can lead to increased incidence of seizures, and increased seizures can lead to an even greater increase in chronic anxiety.

In summation, unexpected seizures can result in accident, injury, embarrassment, and costly trips to the emergency room. They can be difficult to predict and can be dangerous, particularly in instances where the patient is unable to contact family, a friend, or medical personnel when needed. Furthermore, patients often must take daily prophylactic medications that can be toxic and can be accompanied by unpleasant, occasionally life-threatening side effects.

SUMMARY

It is to be understood that this summary is not an extensive overview of the disclosure. This summary is exemplary and not restrictive, and it is intended neither to identify key or critical elements of the disclosure nor delineate the scope thereof. The sole purpose of this summary is to explain and exemplify certain concepts of the disclosure as an introduction to the following complete and extensive detailed description.

Disclosed is a collector for a seizure detection device comprising a collector material configured to collect volatile organic compounds given off from a patient's skin; a wrapping configured to isolate the collector material from an external environment; a heater comprising a heating element, the heating element configured to emit a thermal pulse to desorb the volatile organic compounds from the collector material; and a mesh layer configured to prevent the collector material from contacting the patient's skin, wherein the collector material is received between the wrapping and the mesh layer.

Also disclosed is a seizure detection device comprising a collector comprising a collector material configured to collect volatile organic compounds given off from a patient's skin; a separator comprising a gas chromatography column, the gas chromatography column comprising a chemically-selective film, wherein mixtures of the volatile organic compounds are configured to elute from the collector and to diffuse into and out of the chemically-selective film to separate the mixtures into their constituent chemicals; and an identifier comprising a detector and a processor, the detector configured to receive, ionize, and detect the constituent chemicals eluting from the gas chromatography column, the processor configured to process information about the ionized chemicals to identify volatile organic compounds indicative of a seizure.

Also disclosed is a method of detecting a seizure comprising collecting volatile organic compounds with a collector material of a collector; separating each of the volatile organic compounds into its constituent chemicals with a gas chromatography column; ionizing the constituent chemicals to create ionized chemicals and detecting the ionized chemicals; and analyzing the ionized chemicals to identify seizure-indicative volatile organic compounds.

Various implementations described in the present disclosure may include additional systems, methods, features, and advantages, which may not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

BRIEF DESCRIPTION OF THE DRAWINGS

The features and components of the following figures are illustrated to emphasize the general principles of the present disclosure. Corresponding features and components throughout the figures may be designated by matching reference characters for the sake of consistency and clarity.

DETAILED DESCRIPTION

Figure 1:
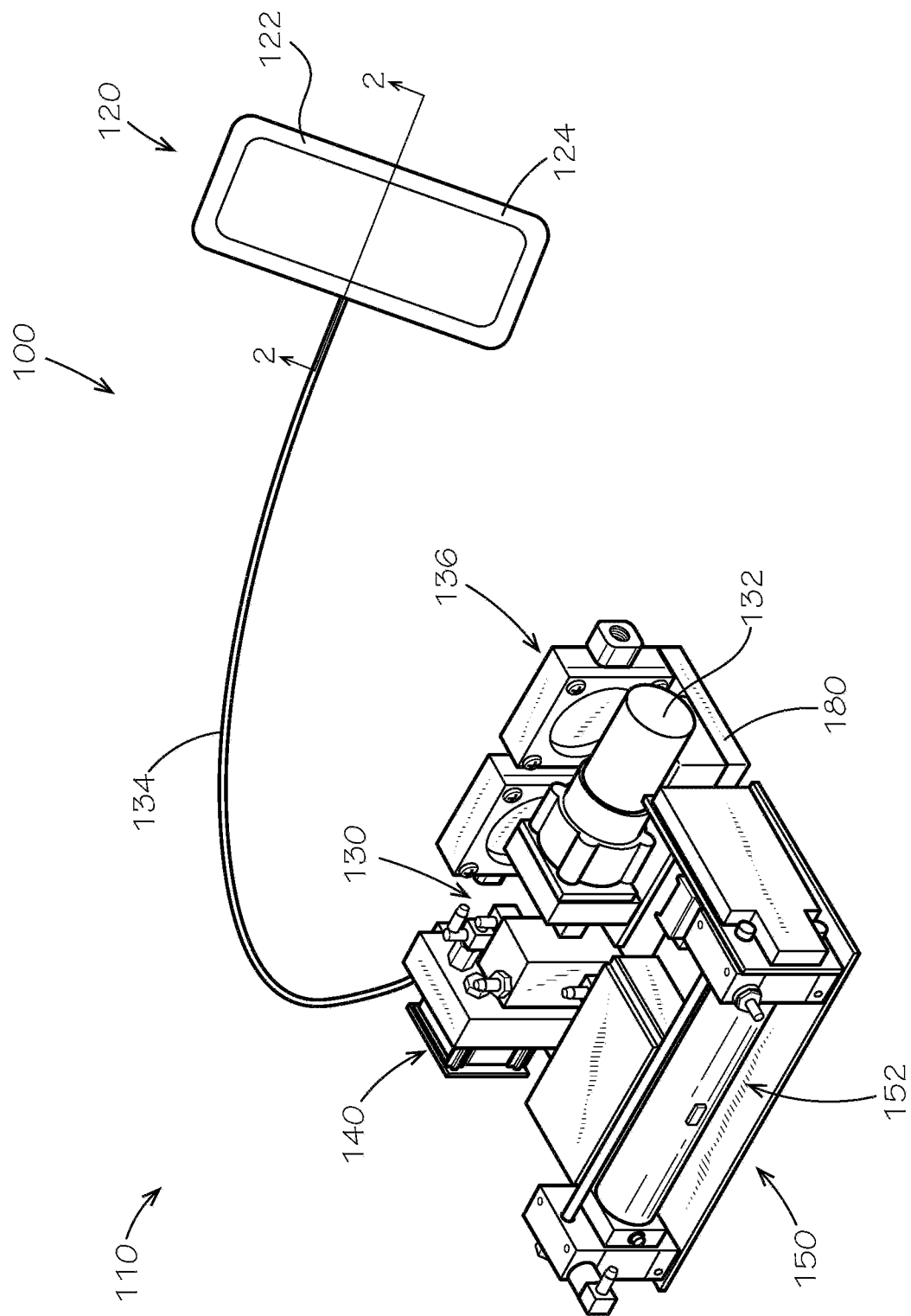
FIG. 1 is a top perspective view of a seizure detection device, in accordance with one aspect of the present disclosure.

The present disclosure can be understood more readily by reference to the following detailed description, examples, drawings, and claims, and the previous and following description. However, before the present devices, systems, and/or methods are disclosed and described, it is to be understood that this disclosure is not limited to the specific devices, systems, and/or methods disclosed unless otherwise specified, and, as such, can, of course, vary. It is also to be understood that the terminology used herein is for the purpose of describing particular aspects only and is not intended to be limiting.

The following description is provided as an enabling teaching of the present devices, systems, and/or methods in its best, currently known aspect. To this end, those skilled in the relevant art will recognize and appreciate that many changes can be made to the various aspects of the present devices, systems, and/or methods described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

As used throughout, the singular forms "a," "an" and "the" include plural referents unless the context clearly dictates otherwise. Thus, for example, reference to "an element" can include two or more such elements unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

For purposes of the current disclosure, a material property or dimension measuring about X or substantially X on a particular measurement scale measures within a range between X plus an industry-standard upper tolerance for the specified measurement and X minus an industry-standard lower tolerance for the specified measurement. Because tolerances can vary between different materials, processes and between different models, the tolerance for a particular measurement of a particular component can fall within a range of tolerances.

As used herein, the terms "optional" or "optionally" mean that the subsequently described event or circumstance can or cannot occur, and that the description includes instances where said event or circumstance occurs and instances where it does not.

The word "or" as used herein means any one member of a particular list and also includes any combination of members of that list. Further, one should note that conditional language, such as, among others, "can," "could," "might," or "may," unless specifically stated otherwise, or otherwise understood within the context as used, is generally intended to convey that certain aspects include, while other aspects do not include, certain features, elements and/or steps. Thus, such conditional language is not generally intended to imply that features, elements and/or steps are in any way required for one or more particular aspects or that one or more particular aspects necessarily include logic for deciding, with or without user input or prompting, whether these features, elements and/or steps are included or are to be performed in any particular aspect.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutations of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific aspect or combination of aspects of the disclosed methods.

Disclosed in the present application is a seizure detection device and associated methods, systems, devices, and various apparatus. Example aspects of the seizure detection device can comprise a collector, a separator, and an identifier. It would be understood by one of skill in the art that the disclosed seizure detection device is described in but a few exemplary aspects among many. No particular terminology or description should be considered limiting on the disclosure or the scope of any claims issuing therefrom.

FIG. 1 illustrates a first aspect of a seizure detection device 100 according to the present disclosure. The seizure detection device 100 can be configured to detect specific seizure-indicative volatile organic compounds (a.k.a. VOCs, and also known as bio-volatile compounds) than can be associated with epileptic seizure onset or occurrence in human patients. For example, the seizure-indicative VOCs can be menthone, menthyl acetate, and/or 3-ethoxy-3,7-dimethyl-1,6-octadiene, which have been identified as seizure biomarkers. In other aspects, the seizure-indicative VOCs can be any other suitable compound that can be associated with seizure in human patients. In some instances, these specific seizure-indicative VOCs may be present, either individually or in any combination, before, during, or after a seizure. Volatile organic compounds (VOCs) 200 (shown in FIG. 2), including the seizure-indicative VOCs, can be emitted as gases from the human patient, for example, through the patient's skin. According to example aspects, the seizure detection device 100 can comprise a sensor device 110 that can detect and analyze VOCs 200 in a three-stage process including pre-concentration (PC), gas chromatography (GC) separation, and detection.

According to example aspects, the sensor device 110 can comprise a collector 120, a separator 130, and an identifier 150. The collector 120 can be formed as a patch 122 that can contact the patient's skin 270 (shown in FIG. 2). In one aspect, the patch 122 can be adhered to the skin 270 by an adhesive. In another aspect, the patch 122 can be applied by another fastener, such as a band or tie, or any other suitable fastener known in the art. In the pre-concentration state, the collector 120 can collect target chemicals (e.g., VOCs 200) from the environment and can reject interferents. In the present aspect, the collector 120 can comprise a chemically-clean wrapping 124 that can isolate a collector material 226 (shown in FIG. 2) from possible external environmental contaminants. The collector material 226 can be configured to collect VOCs 200 given off as a gas from the patient's skin 270, in some aspects, and may also collect other compounds. The collector material 226 can also be isolated from direct physical contact with the patient's skin 270 to minimize contamination by sweat or skin bacteria, as described in further detail below with respect to FIG. 2. According to example aspects, a heater 228 (shown in FIG. 2) can be integrated with the collector material 226 and a thermal pulse from the heater 228 can desorb the VOCs 200 (and possibly other compounds) from the collector material 226. A pump 132 of the seizure detection device 100 can then pump the desorbed VOCs 200 through a transfer tube 134 to the separator 130.

In the GC separation stage, the collected VOCs 200 can be injected into a carrier gas (not shown), such as, for example, helium or nitrogen. A small gas plug (e.g., a sample of the carrier gas and VOC mixture) can be injected into a long, rectangular flow column (not shown) of the separator 130. According to example aspects, a valve 140 can control injection of the gas plug and the direction and flow of the gas plug through the column. Example aspects of the column can be a µGC (micro gas chromatography) column, while in other aspects, the column can be a conventional GC (gas chromatography) column. In some aspects, the column can be similar to any of the aspects disclosed in U.S. Pat. No. 10,151,732, filed Jan. 11, 2016, U.S. Pat. No. 6,699,392, filed Jun. 10, 2002, and U.S. Pat. No. 6,666,907, filed Jan. 31, 2002 which are hereby incorporated by reference herein in their entireties. In some aspects, the gas plug can undergo a µGC×GC separation or a conventional GC×GC separation, which can allow for high-fidelity separations and ultra-low false alarm rates. µGC×GC separation is micro gas chromatography x micro gas chromatography separation, while GC×GC separation is a conventional gas chromatography x gas chromatography separation, both of which can also be known as two-dimensional gas chromatography.

According to example aspects, the column can be coated with a chemically-selective film, and the chemically-selective film can be referred to as a stationary phase. As the gas plug flows through the column, individual chemicals from the gas plug (including individual chemicals of the VOCs 200) diffuse into and out of the stationary phase based on their solubility within the stationary phase. VOCs 200 with a low solubility can quickly flow through the channel, while VOCs 200 with high solubility can spend a relatively long time within the stationary phase. This time-delay separates the complex chemical mixture of the gas plug into its constituent chemicals and introduces valuable spatial and chemical information that is critical for positive chemical identification and false alarm reductions in the detection stage. In example aspects, the column can be a silicon µGC column that can be about 160 cm in length, about 65 µm in width, and about 650 µm deep. In example aspects, heaters (e.g., metal heaters) (not shown) can be integrated with the silicon µGC column. Furthermore, the high aspect ratio silicon µGC column can fit on a die 136 that can be about 2 cm by 2 cm on each side of the die 136, which can be a significant size reduction in comparison to traditional columns. According to example aspects, the reduced size can allow for a µGC separation to be performed in under 30 seconds by heating the column from 70-200+° C. at an average power of 4.5 W.

Finally, in the detection stage, the identifier 150 can sense the chemicals eluting from the column and can transduce the chemical information to a recordable signal. For example, the identifier 150 can comprise an Ion Mobility Spectrometer (IMS) detector 152. In a particular aspect, the IMS detector 152 can be a CIMS (Correlation Ion Mobility Spectrometer) detector. In another particular aspect, the IMS detector 152 can be a LTCC (Low Temperature Co-fired Ceramic) CIMS detector. In other aspects, the detector 150 can comprise a flame ionization detector (FID), a photoionization detector (PID), a pulsed discharge ionization detectors (PDID), a resonator-based detector including quartz crystal micro balances, surface acoustic wave detectors, and/or micro-fabricated cantilever based resonators, a chemiresistor, a chemicapacitor, a thermal conductivity detector (TCD), a spectroscopic detector including vacuum ultra violet (VUV), ultraviolet, visible, and/or infrared radiation detection, a mass spectrometer detection method (MS), a non-gas chromatographic separation method such as IMS (ion mobility spectrometry), IMS-MS (ion mobility spectrometry-mass spectrometry), and/or MS-MS (tandem mass spectrometry), or any other suitable detector known in the art. Within the IMS detector 152, the incoming chemicals can be ionized and pulled down an IMS drift tube (not shown) by a potential gradient. In some aspects, the IMS drift tube can be similar to the drift tube disclosed in U.S. Pat. No. 7,155,812, filed Sep. 4, 2003, which is hereby incorporated by reference herein in its entirety.

Because the IMS detector 152 can operate at atmospheric pressures, the ionization of the chemicals can be considered a "soft" ionization, in that it minimizes the breakup or fragmentation of the chemicals. The ionized chemicals (also known as ions) can be drawn into the IMS drift tube, and the IMS drift tube can contain a faraday cup detector (not shown) at an end thereof that can count the ionic charge. The speed at which an ion travels down the IMS drift tube is a function of the ion's size, charge, and the interactions between the ion and other molecules in the IMS drift tube. Careful measurement of a characteristic transit speed down the IMS drift tube, called a reduced mobility value (or $K_o$), of a parent ion and its adducts can positively identify the target species (e.g., the specific seizure-indicative VOCs associated with seizures). In example aspects, the seizure detection device 100 can comprise a processor (not shown), for example, on a printed circuit board (PCB), for processing the data and determining whether one or more of the seizure-indicative VOCs is present. According to example aspects, a battery 180, such as a lithium ion battery, or another power source can be provided for powering the sensor device 110, including the processor.

When detection of one or more of the seizure-indicative VOCs is made, or detection of a significant concentration of one or more of the seizure-indicative VOCs is made, the processor can activate a signal. In some aspects, the signal can sound an immediate alarm to alert a patient that a seizure may be imminent. In some aspects, the signal can also or alternatively be sent wirelessly (e.g., via Bluetooth) to an external receiving unit, such as an application (also known as an app) on a cellular phone, smartphone, tablet, or other electronic instrument, to activate an additional alarm. In some instances, there can be enough forewarning to introduce an abortive therapy for the oncoming seizure. Furthermore, in some aspects, the seizure detection device 100 can also alert a caregiver or emergency personnel. Memory can be included in the application and/or the device 100 itself that can profile levels of seizure-indicative VOC concentration, duration, and the time and date of occurrence. This data can then be used as a diary of seizure activity for later review by the patient or a physician. In some aspects, the data can also be used to better predict future seizures based on the patient's individual chemistry pre-seizure. For example, in one aspect, the seizure detection device 100 may detect a slightly elevated concentration of menthone in the patient before multiple seizure occurrences. The processor can analyze this data to detect the pattern of increased menthone pre-seizure, and can identify increased menthone as a seizure-indicative VOC in the patient. The seizure detection device 100 can then alert the patient any time menthone, or a significant concentration of menthone, is detected.

Figure 2:
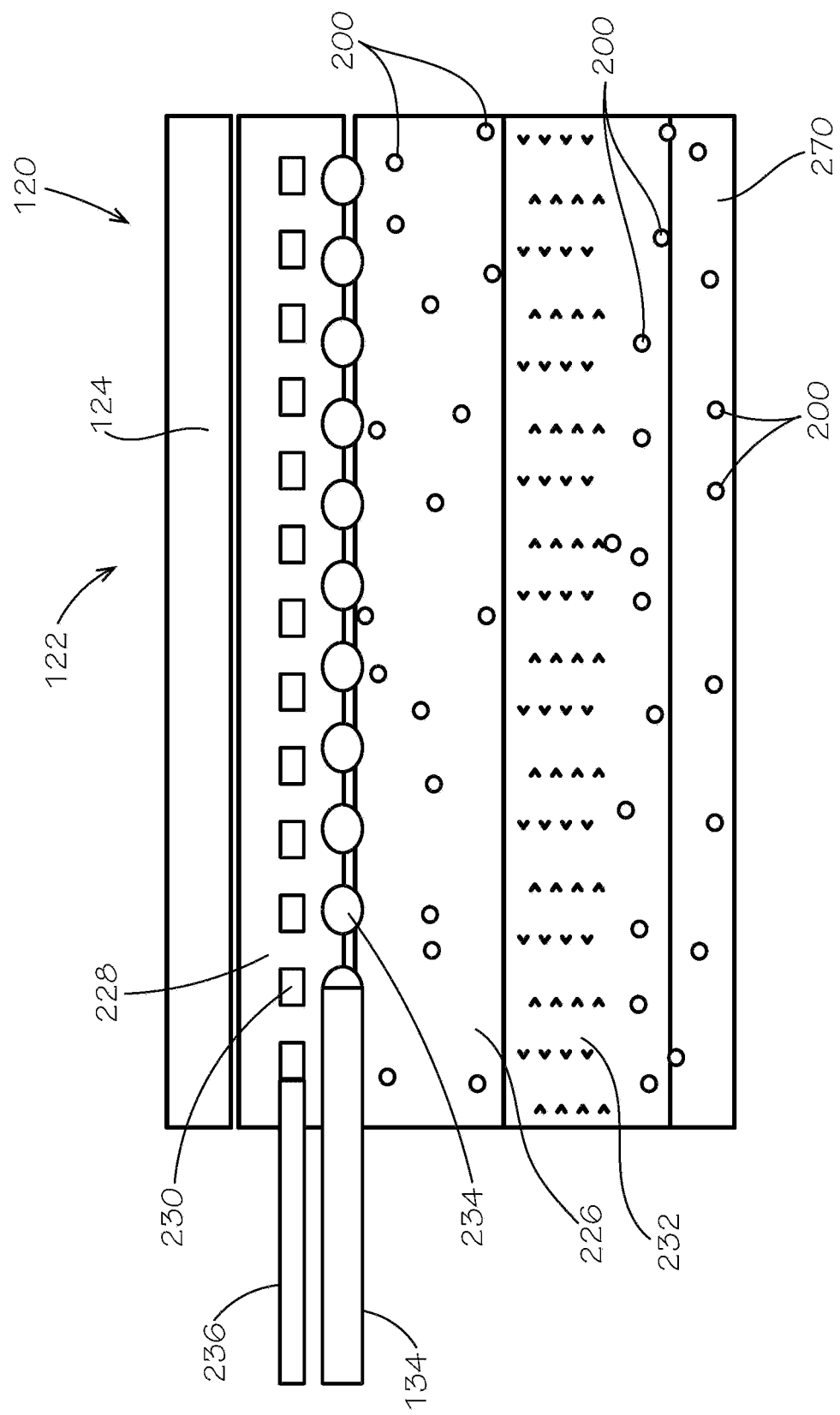
FIG. 2 is a cross-sectional view of a collector of the seizure detection device of FIG. 1, taken along line 2-2 of FIG. 1.

FIG. 2 illustrates a cross-sectional view of the collector 120 taken along line 2-2 of FIG. 1. As shown, the collector 120 can be applied to the skin 270 of a patient. The chemically-clean wrapping 124 can define an outer layer of the collector 120. In some aspects, the chemically-clean wrapping 124 can be a polyimide film, and in the present aspect, the wrapping 124 can be a polyimide film with a silicone adhesive. In other aspects, any other suitable adhesive or other fastener can be used. The collector material 226 can define an intermediate layer of the collector 120, and in the present aspect, the collector material 226 can be formed from PDMS (polydimethylsiloxane), which is a type of silicone, for example and without limitation. In the present aspect, the heater 228 can be attached to the wrapping 124, and can be positioned between the wrapping 124 and the collector material 226, as shown. In other aspects, the heating element of the heater 228 can be integrated with the wrapping 124. Furthermore, a mesh 232 can define an inner layer of the collector 120 and can be positioned between the collector material 226 and the patient's skin. Example aspects of the mesh can be formed from a polymer, such as polytetrafluoroethylene (PTFE). In other aspects, the mesh can be formed from a metal material or any other suitable material known in the art. The mesh 232 can prevent the collector material 226 from contacting the patient's skin and being contaminated by sweat, oils, and bacteria from the skin, and/or other undesirable elements.

In other aspects, the collector 120 can be configured to collect VOCs 200 through a patient's sweat, saliva, breath (e.g., exhalation), or any other suitable bodily process. Also in other aspects, the seizure-indicative VOCs can further or alternatively include β-bourbonene, β-cubebene, or any other suitable VOC that may be identified as a seizure biomarker. Furthermore, in some aspects, instead of being in contact with the patient's skin, the collector can be positioned near the patient (e.g., next to a patient's chair or bed, or elsewhere in a patient's room) and can be configured to collect VOCs from the ambient air surrounding the patient, which have been released into the air through the patient's skin and/or through the patient's exhalation.

Example aspects of the heater 228 can comprise a heating coil 230 configured to emit a thermal pulse, which can desorb VOCs 200 received in the collector material 226 into a flow channel(s) 234 between the heating coil 230 and the collector material 226. In example aspects, a power cord 236 can be connected to the heater 228 to provide power to the heating coil 230. In some aspects, the power cord 236 can be connected to the battery 180 or other power source to transfer power to the heating coil 230. When the VOCs 200 are desorbed from the collector material 226 and into the flow channel 234, the pump 132 can then sweep the VOCs 200 out of the flow channel 234 and through the transfer tube 134 to the separator 130 (shown in FIG. 1).

The seizure detection device 100 can allow patients to position themselves such that they can avoid accident, injury, embarrassment, and unnecessary trips to the emergency room. In some aspects, the seizure detection device 100 can also alert families, friends, and medical personnel to oncoming seizures, potentially reducing the amount of prophylactic medications need by patients on a daily basis. As many of these medications can be toxic and accompanied by unpleasant, occasionally life-threatening side effects, any reduction in daily dosage can result in vast improvements in patient wellbeing and functionality. Furthermore, the predictive seizure detection device 100 can allow for the development of rescue protocols in some aspects, which could reduce the severity of an oncoming seizure or, in some instances, prevent onset altogether, thus reducing or avoiding the damage that seizures can cause to the brain and the body of the patient.

Evidence indicates the presence of these seizure-indicative VOCs during the preictal (i.e., pre-seizure) stage, building in different patients at different times and at different levels of concentration based on the individual patient's metabolism and blood chemistry. Consequently, the timing of a predictive alert issued by the seizure-protection device 100 can necessarily vary from patient to patient. As a form of reference, the seizure-indicative VOCs can remain in the patient's system anywhere from about five to forty minutes postictal (i.e., post-seizure) based on the individual's metabolism.

Example aspects of the seizure detection device 100 can be on a small enough scale that the seizure detection device 100 can be easily transported with a patient as they go about daily activities, including working, exercising, eating, and sleeping. As such, various elements of the seizure detection device 100 (e.g., the column, the processor, etc.) can be formed as miniature or micro versions of such elements.

One should note that conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more particular embodiments or that one or more particular embodiments necessarily include logic for deciding, with or without user input or prompting, whether these features, elements and/or steps are included or are to be performed in any particular embodiment.

It should be emphasized that the above-described embodiments are merely possible examples of implementations, merely set forth for a clear understanding of the principles of the present disclosure. Any process descriptions or blocks in flow diagrams should be understood as representing modules, segments, or portions of code which include one or more executable instructions for implementing specific logical functions or steps in the process, and alternate implementations are included in which functions may not be included or executed at all, may be executed out of order from that shown or discussed, including substantially concurrently or in reverse order, depending on the functionality involved, as would be understood by those reasonably skilled in the art of the present disclosure. Many variations and modifications may be made to the above-described embodiment(s) without departing substantially from the spirit and principles of the present disclosure. Further, the scope of the present disclosure is intended to cover any and all combinations and sub-combinations of all elements, features, and aspects discussed above. All such modifications and variations are intended to be included herein within the scope of the present disclosure, and all possible claims to individual aspects or combinations of elements or steps are intended to be supported by the present disclosure.

That which is claimed is:

1. A method of detecting a seizure comprising:
providing a seizure detection device, the seizure detection device comprising a collector, a separator, and an identifier; wherein the collector is formed as a patch;
adhering the patch to the user's skin with an adhesive;
collecting volatile organic compounds released into the air from a user's skin with a collector material of the collector, the collector applied to the user's skin, the collector material disposed between the user's skin and an outer layer of the collector, the outer layer isolating the collector material from an external environment, wherein the collector further comprises an inner layer positioned between the collector material and the user's skin, wherein the inner layer extends fully and continuously along a length of the collector material between the user's skin and the collector material, wherein the length of the collector material is defined between a first side of the collector material and an opposite second side of the collector material, and wherein the inner layer prohibits sweat from the user's skin from contaminating the collector material;
heating the collector material to desorb the volatile organic compounds from the collector material, the collector comprising a heater for heating the collector material; wherein heating the collector to desorb the volatile organic compounds from the collector material comprises desorbing the volatile organic compounds from the collector material into a flow channel, the flow channel oriented between the collector material and the outer layer;
transferring the volatile organic compounds from the flow channel to a transfer tube; and transferring the volatile organic compounds through the transfer tube from the collector to the separator; and wherein the separator and the identifier are indirectly attached to the patch by the transfer tube;
separating a mixture of the volatile organic compounds into its constituent chemicals with a gas chromatography column of the separator;
ionizing the constituent chemicals to create ionized chemicals and detecting the ionized chemicals;
analyzing the ionized chemicals with a processor of the identifier to identify seizure indicative volatile organic compounds; and
transporting the seizure detection device, including the collector, the separator, and the identifier, with the user as the user goes about daily activities.

2. The method of claim 1, wherein heating the collector material to desorb the volatile organic compounds from the collector material comprises emitting a thermal pulse from the heater to desorb the volatile organic compounds from the collector material.

3. The method of claim 2, wherein the heater is a heating coil, the method further comprising providing power to the heating coil.

4. The method of claim 1, further comprising transferring the volatile organic compounds from the collector to the gas chromatography column.

5. The method of claim 4, wherein transferring the volatile organic compounds from the collector to the gas chromatography column comprises pumping the volatile organic compounds through a transfer tube.

6. The method of claim 1, wherein separating a mixture of the volatile organic compounds into its constituent chemicals with a gas chromatography column comprises diffusing the volatile organic compounds into and out of a chemically-selective film of the gas chromatography column.

7. The method of claim 6, wherein separating a mixture of the volatile organic compounds into its constituent chemicals with a gas chromatography column further comprises heating the gas chromatography column.

8. The method of claim 1, further comprising injecting the volatile organic compounds into a carrier gas to form a gas plug and injecting the gas plug into the gas chromatography column.

9. The method of claim 1, wherein the steps of ionizing the constituent chemicals to create ionized chemicals and detecting the ionized chemicals and analyzing the ionized chemicals to identify seizure-indicative volatile organic compounds are performed by a detector.

10. The method of claim 9, wherein the detector is an Ion Mobility Spectrometer (IMS) detector.

11. The method of claim 10, wherein analyzing the ionized chemicals to identify seizure-indicative volatile organic compounds comprises drawing the ionized chemicals into a drift tube of the IMS and counting an ionic charge of the ionized chemicals at an end of the drift tube.

12. The method of claim 1, wherein analyzing the ionized chemicals to identify seizure-indicative volatile organic compounds comprises calculating a reduced mobility value of the ionized chemicals with the processor.

13. The method of claim 1, further comprising generating a signal related to the seizure-indicative volatile organic compounds with the processor.

14. The method of claim 13, wherein generating the signal related to the seizure-indicative volatile organic compounds with the processor comprises generating an alert when a concentration of the seizure-indicative volatile organic compounds is detected.

15. The method of claim 1, wherein the inner layer is a mesh layer.

16. The method of claim 1, wherein the seizure-indicative volatile organic compounds comprise at least one of menthone, menthyl acetate, and 3-ethoxy-3,7-dimethyl-1,6-octadiene.

17. The method of claim 15, wherein the mesh layer comprises a metal material.

18. The method of claim 15, wherein the mesh layer comprises a polymer.

19. The method of claim 18, wherein the polymer is polytetrafluoroethylene.

20. The method of claim 1, wherein:
the seizure detection device further comprises a band; and
the method further comprises attaching the collector to the user with the band.

* * * * *